(12) United States Patent
Lacey et al.

(10) Patent No.: US 10,987,475 B2
(45) Date of Patent: Apr. 27, 2021

(54) SYSTEMS FOR FEEDBACK CONTROL OF ANESTHETIC AGENT CONCENTRATION (71) Applicant: General Electric Company, Schenectady, NY (US)

(72) Inventors: Joseph James Lacey, Cambridge, WI (US); David Michael Wahl, Madison, WI (US); Thomas Lane Bender, II, Cottage Grove, WI (US); Russell James Kuzelka, McFarland, WI (US)

(73) Assignee: General Electric Company, Schenectady, NY (US)

( * ) Notice: Subject to any disclaimer, the term of this patent is extended or adjusted under 35 U.S.C. 154(b) by 536 days.

(21) Appl. No.: 15/793,696

(22) Filed: Oct. 25, 2017

(65) Prior Publication Data

US 2019/0117920 A1 Apr. 25, 2019

(51) Int. Cl.
*A61M 16/01* (2006.01)
*A61M 16/00* (2006.01)
(Continued)

(52) U.S. Cl.
CPC ........ *A61M 16/01* (2013.01); *A61M 16/0093* (2014.02); *A61M 16/104* (2013.01);
(Continued)

(58) Field of Classification Search
CPC .. A61M 16/00; A61M 16/01; A61M 16/0093; A61M 16/104; A61M 16/18;
(Continued)

(56) References Cited

U.S. PATENT DOCUMENTS 5,471,979 A 12/1995 Psaros et al.
5,505,236 A * 4/1996 Grabenkort ......... A61M 16/183
128/202.27
(Continued)

FOREIGN PATENT DOCUMENTS

EP 0894506 A2 2/1999
EP 0911052 A2 4/1999
(Continued)

OTHER PUBLICATIONS

Translation of JP-2004/236874. Accessed on Espacenet. (Year: 2004).*

*Primary Examiner* — Valerie L Woodward
*Assistant Examiner* — Paige Kathleen Bugg
(74) *Attorney, Agent, or Firm* — McCoy Russell LLP (57) ABSTRACT

Methods and systems are provided for delivering anesthetic agent to a patient. In one embodiment, a system includes an anesthetic agent reservoir, a pump fluidically coupled to the agent reservoir, an injector configured to receive pressurized anesthetic agent from the pump, a vaporizer comprising a heated chamber configured to receive and vaporize the anesthetic agent injected by the injector and supply a mix of the vaporized anesthetic agent and medical gas to a subject via a supply line, and a controller. The controller stores instructions executable to determine a concentration of the vaporized anesthetic agent in the mix and adjust one or more injector parameters based on a difference between the concentration of the vaporized anesthetic agent and a commanded concentration.

17 Claims, 4 Drawing Sheets

(51) Int. Cl.
*A61M 16/18* (2006.01)
*A61M 16/10* (2006.01)
*A61M 16/20* (2006.01)

(52) U.S. Cl.
CPC .......... *A61M 16/18* (2013.01); *A61M 16/0057* (2013.01); *A61M 16/183* (2013.01); *A61M 16/202* (2014.02); *A61M 2016/0027* (2013.01); *A61M 2016/0033* (2013.01); *A61M 2016/1035* (2013.01); *A61M 2202/0208* (2013.01); *A61M 2202/0283* (2013.01); *A61M 2205/3331* (2013.01); *A61M 2205/3334* (2013.01); *A61M 2205/3355* (2013.01); *A61M 2205/3365* (2013.01); *A61M 2205/3368* (2013.01)

(58) Field of Classification Search
CPC ............ A61M 16/202; A61M 16/0057; A61M 16/183; A61M 16/0003; A61M 16/0069; A61M 16/022; A61M 16/024; A61M 16/20; A61M 16/201; A61M 16/204; A61M 15/00; A61M 15/002; A61M 15/0015; A61M 15/0016; A61M 2016/0027; A61M 2016/0033; A61M 2016/1035; A61M 2016/003; A61M 2202/0208; A61M 2202/0241; A61M 2202/0283; A61M 16/12; A61M 16/122; A61M 16/14; A61M 16/147
USPC ........................................ 128/203.12, 203.14
See application file for complete search history.

(56) References Cited

U.S. PATENT DOCUMENTS

| | | | |
|---|---|---|---|
| 5,546,931 | A | 8/1996 | Rusz |
| 5,931,160 | A | 8/1999 | Gilmore et al. |
| 7,032,595 | B2 | 4/2006 | Bunke et al. |
| 9,370,636 | B2 | 6/2016 | Larsson et al. |
| 9,988,954 | B2 * | 6/2018 | Macfarlane .............. F01M 1/16 |
| 2004/0060999 | A1 | 4/2004 | Kock |
| 2005/0081830 | A1 * | 4/2005 | Yu ........................ F02M 59/462 123/510 |
| 2012/0031402 | A1 | 2/2012 | Loncar et al. |
| 2013/0276782 | A1 * | 10/2013 | Larsson .............. A61M 16/147 128/203.14 |
| 2015/0059744 | A1 * | 3/2015 | Fisher .................... A61B 5/087 128/203.14 |
| 2015/0165140 | A1 * | 6/2015 | Cappelli ........... A61M 16/0051 128/204.21 |
| 2016/0008567 | A1 * | 1/2016 | Bottom ................ A61M 16/20 128/200.23 |
| 2016/0341165 | A1 * | 11/2016 | Ishikawa ............ F02M 61/1813 |
| 2019/0151584 | A1 * | 5/2019 | Kuck .................... A61M 16/01 |
| 2019/0275273 | A1 * | 9/2019 | Chang ............... A61M 16/0066 |

FOREIGN PATENT DOCUMENTS

| | | | |
|---|---|---|---|
| JP | 2004236874 A | * | 8/2004 |
| WO | 2006009498 A1 | | 1/2006 |

* cited by examiner

SYSTEMS FOR FEEDBACK CONTROL OF ANESTHETIC AGENT CONCENTRATION

FIELD

Embodiments of the subject matter disclosed herein relate to delivery of anesthetic agent, and more particularly, to closed-loop feedback control of delivered vaporized anesthetic agent.

BACKGROUND

In order to perform surgery on a patient, an inhaled anesthetic agent may be supplied to the patient to provide temporary anesthesia to enable surgery and eliminate patient discomfort. The concentration of the anesthetic agent may be controlled to ensure sufficient anesthetic agent is provided for patient comfort without compromising patient safety. A traditional method for supplying anesthetic agent has been to absorb the liquid agent into a wick material and pass patient gas over the wick to evaporate the agent, which is controlled by the amount of gas flowing past the wick.

BRIEF DESCRIPTION

In one embodiment, a system includes an anesthetic agent reservoir, a pump fluidically coupled to the agent reservoir, an injector configured to receive pressurized anesthetic agent from the pump, a vaporizer comprising a heated chamber configured to receive and vaporize the anesthetic agent injected by the injector and supply a mix of the vaporized anesthetic agent and medical gas to a subject via a supply line, and a controller. The controller stores instructions executable to determine a concentration of the vaporized anesthetic agent in the mix and adjust one or more injector parameters based on a difference between the concentration of the vaporized anesthetic agent and a commanded concentration.

In this way, the amount of anesthetic agent provided to a patient may be precisely controlled by measuring the concentration of the agent in the gas supplied to the patient and then adjusting a frequency and/or duration of injections based on the concentration of the agent. Additionally, the pump outlet pressure may be varied, which in combination with the frequency and duration of the injections determined the agent flow rate. Further, by supplying pressurized agent to the injector via the pump, the agent reservoir is not pressurized (other than the natural vapor pressure of the agent), thus allowing refills of the reservoir without disrupting the delivery of the anesthetic agent during a medical procedure.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of an anesthetic agent delivery system. In particular, systems and methods are provided for feedback control of an injected anesthetic agent. The anesthetic agent may be supplied to an injector via a pump and the injector may inject the supplied agent to a vaporizer, where the agent may vaporize and mix with medical gas before being supplied to a patient. The concentration of the agent in the medical gas supplied to the patient may be measured by a sensor, and the output of the sensor may be provided as feedback to a closed-loop control system to adjust the amount of agent injected by the injector. In doing so, the amount of agent supplied to the patient may be controlled automatically, reducing waste of the agent and ensuring a desired amount of agent is supplied to the patient. Additionally, by monitoring agent pressure at the injector inlet, the injection frequency, and the injection duration (also referred to as the injector on time), the agent flow rate may be estimated. The concentration of the agent may be estimated based on the medical gas flow rate and the agent flow rate. This estimate may be used to allow operation if the agent concentration sensor is operating with reduced performance (e.g., degraded) and also serves as a safety check on agent concentration measurements.

Figure 1:
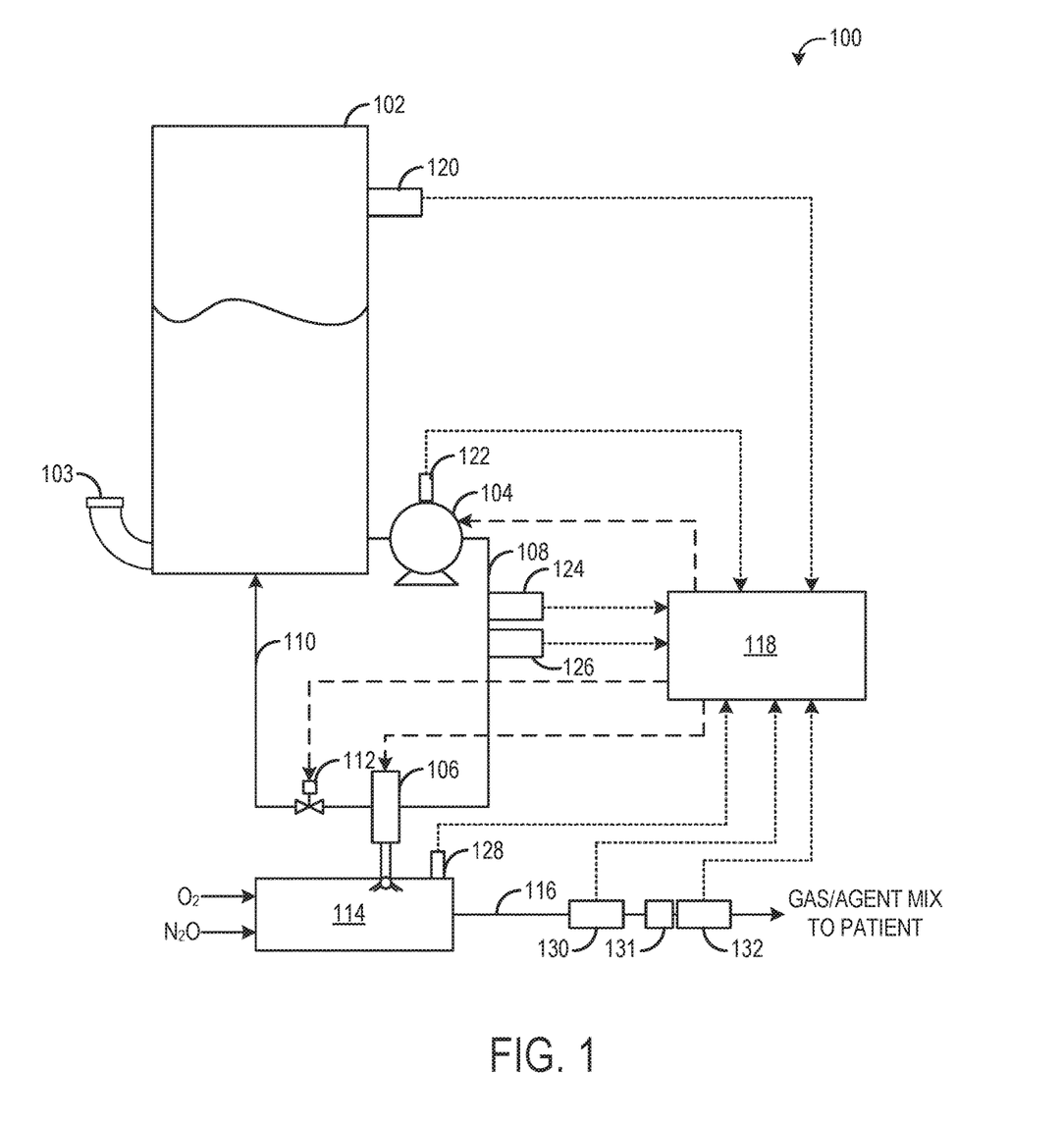
FIG. 1 schematically shows an example anesthetic agent delivery system.

Referring now to FIG. 1, a schematic view of an anesthetic agent delivery system 100 according to an embodiment of the present disclosure is shown. The system 100 may be used in surgery and other medical procedures to maintain a partially closed breathing environment for the patient, through which a controlled and medically appropriate amount of anesthetic, in the form of a gas, may be administered.

System 100 includes an anesthetic agent reservoir 102 configured to store a suitable liquid anesthetic agent. Agent reservoir 102 is fluidically coupled to a pump 104. Pump 104, when activated, pumps liquid anesthetic agent from agent reservoir 102 to an agent injector 106 via a liquid agent supply line 108. Injector 106 may include a rail or be coupled to a rail, in order to allow agent to in the rail to be pressurized to enable high-pressure injection of the liquid agent. Liquid anesthetic agent that is not injected via the injector 106 returns to agent reservoir 102 via return line 110. An agent flow control device 112 may be positioned in return line 110. Agent flow control device 112 may be configured to adjust the flow rate of liquid agent returned to agent reservoir 102, thereby adjusting a pressure of the liquid agent at the injector 106. Agent flow control device 112 may be a valve, a multi-ported restrictor (e.g., fixed size orifices, Jeweled orifices, multi-sized orifices), or other suitable device. For example, the flow control device may include a cone that has several different sized holes drilled in it which changes pressure and flow characteristics based on pump speed.

Pump 104 may be a suitable pump. In one example, pump 104 may be a reciprocating pump, such as an axial or radial piston, or a multistage pump. Pump 104 may draw liquid agent from agent reservoir 102 and supply pressurized liquid agent to liquid agent supply line 108. Due to the reciprocating nature of the pump, which may cause pressure pulsations at injector 106, an accumulator (not shown) may be present upstream of injector 106. In other examples, liquid agent supply line 108 may be comprised of a stretchable material or otherwise be configured to act as an accumulator and/or system compliance may be present in the rail or in front of the injector.

Due to the pump supplying pressurized liquid agent to the rail and then to injector 106 and/or to just injector 106, the liquid agent in agent reservoir 102 may be maintained at an unregulated pressure. As such, agent reservoir 102 may not be pressurized above atmospheric pressure (e.g., vapor pressure) via an external pressure supply (although the pressure in agent reservoir 102 may change relative to atmospheric pressure due to natural pressure or vacuum resulting from temperature fluctuations, vaporization of the liquid agent, or agitation of the liquid agent). Thus, when a level of the liquid agent in agent reservoir 102 falls below a threshold, the liquid agent may be refilled without depressurizing agent reservoir 102. Further, in some examples, an interface 103 may be present for communicating liquid anesthetic agent from a commercial container (not shown) (e.g., the container of liquid anesthetic agent supplied by the liquid anesthetic agent manufacturer) to the anesthetic agent reservoir 102 in an automated fashion, e.g., such that the reservoir does not have to be filled manually by an operator. The interface 103 may include a quick connect (e.g., quarter turn connect) on the reservoir or fluidically coupled to the reservoir (e.g., via a passage, as shown in FIG. 1), where the connect is configured to couple to a corresponding connector of the liquid anesthetic agent container. The liquid anesthetic agent stored in the commercial container may then be supplied to the reservoir (e.g., via gravity) and once the commercial container is empty, the container may be replaced with a new, full commercial container. Such a configuration may prevent operator exposure to the liquid anesthetic agent. In still further examples, the liquid anesthetic agent commercial container may itself be the liquid agent reservoir, e.g., the liquid anesthetic agent commercial container may include a connector that is configured to fluidically couple to the pump.

Injector 106 is coupled to a vaporizer 114. When activated, injector 106 supplies liquid anesthetic agent into a chamber of vaporizer 114. Injector may be a suitable injector, such as a piezoelectric or solenoid injector. Injector 106 may inject liquid anesthetic agent via a plurality of nozzle holes or other suitable arrangement in order to atomize the liquid anesthetic agent to promote vaporization.

Vaporizer 114 may comprise a chamber that is heated in order to promote vaporization of the injected anesthetic agent. The chamber of vaporizer 114 may be heated via a heat source (such as an electric heater or gas burner) positioned internally or externally to the chamber, via a heat transfer fluid jacket, or other suitable mechanism. Vaporizer 114 may include one or more gas ports to receive pressurized medical gas, which may include oxygen, nitrous oxide, fresh air, and/or other gases.

The injected anesthetic agent vaporizes in vaporizer 114 and mixes with the supplied medical gas. Due to the characteristics of the pressurized medical gas, the vaporized agent and medical gas mix flows out of the vaporizer via an exit port and is supplied to a patient via a supply line 116. While not shown in FIG. 1, it is to be understood that supply line 116 may be coupled to a suitable patient delivery mechanism, such as an anesthesia machine mouthpiece or endotracheal tube.

System 100 further includes a controller 118. Controller 118 includes a processor operatively connected to a memory. The memory may be a non-transitory computer-readable medium and may be configured to store computer executable code to be processed by the processor in order to execute one or more routines as described herein. The memory may also be configured to store data received by the processor.

Controller 118 is configured to receive and process data. Data may be input by a user via a user input device that is operationally connected to the processor. The user input device may include a mouse, a keyboard, a voice input device, a touch input device for receiving a gesture from a user, a motion input device for detecting non-touch gestures and other motions by a user, and other comparable input devices and associated processing elements capable of receiving user input from a user, or a combination thereof. Controller 118 may be operatively connected to other computing devices, such as hospital computing devices (e.g., PACS, electronic medical record-storing devices, operating room workstations, and/or anesthesia delivery machines).

Controller 118 is configured to receive output from a plurality of sensors of system 100. As shown, controller 118 is operably coupled to an agent reservoir pressure sensor 120 that measures a pressure of agent reservoir 102 as well as pump speed sensor 122 that measures a speed of pump 104. Controller 118 is operably coupled to a liquid agent supply pressure sensor 124 and a liquid agent supply temperature sensor 126, which measure pressure and temperature, respectively, of the pressurized liquid agent supplied to injector 106. Controller 118 is operatively coupled to vaporizer pressure sensor 128 that measures a pressure of the agent/medical gas in the chamber of vaporizer 114. Additionally, controller 118 is operatively coupled to gas sensor(s) positioned in supply line 116. The gas sensors shown in FIG. 1 include a gas flow sensor 130 that measures a flow rate of the vaporized anesthetic agent/medical gas mix, a gas temperature sensor 131 that measures a temperature of the anesthetic agent/medical gas mix, and an agent concentration sensor 132 that measures a concentration of the vaporized anesthetic agent in the vaporized anesthetic agent/medical gas mix. However, in some embodiments the gas flow, temperature, and agent concentration sensors may be combined in one or two sensing units (e.g., the temperature sensor may be combined in a single unit with the concentration sensor) or the gas flow sensor may be dispensed with.

Controller 118 is configured to process the output received by the plurality of sensors and adjust one or more actuators of system 100 in response to the received output. The one or more actuators that may be adjusted by controller 118 include pump 104, agent flow control device 112, and injector 106. For example, controller 118 may send a speed command to pump 104 that controls the speed of the pump to a target speed. Controller 118 may send a valve position command to agent flow control device 112 that controls a position (e.g., degree of opening) of agent flow control device 112. Controller 118 may send one or more injector parameter commands that control a duty cycle and/or valve position (e.g., degree of opening) of injector 106.

In this way, controller 118 may adjust one or more of the speed of the pump and the pressure/flow rate of liquid anesthetic agent in liquid agent supply line 108 and return line. In doing so, the pressure drop across injector 106 may be controlled. Further, controller 118 may adjust an amount of anesthetic agent supplied to vaporizer 114 via injector 106. As explained in more detail below, the pump, agent flow control device, and/or injector may be controlled based on feedback from agent concentration sensor 132 in order to precisely meter a commanded concentration of the anesthetic agent to a patient.

In some examples, the flow rate of the supplied medical gas may be maintained at a fixed rate. In other examples, the flow rate of the supplied medical gas may be adjusted, for example based on feedback from gas flow sensor 130, to account for differences in breathing volume/rate of the patient. The flow rate of the medical gas may be adjusted by controller 118 or another suitable device. Likewise, the heating element of vaporizer 114 may be maintained at a fixed temperature by controller 118 or by a temperature control device associated with the heating element. The fixed temperature may be based on the type of anesthetic agent in the vaporizer, as different anesthetic agents have different boiling temperatures. In other examples, the heating element temperature may be adjusted based on output from the agent concentration sensor. For example, if the agent concentration sensor indicates a lower than expected concentration of anesthetic agent in the mix being supplied to the patient, insufficient vaporization may be occurring and the temperature of the heating element may be increased.

Thus, system 100 described herein system uses a liquid pump to pull liquid agent from the reservoir sump through a loop passing back into the sump. The injector is connected into the loop and when the injector is opened, some of the liquid in the loop flows through the injector valve where the liquid is mixed into the patient medical gas stream. As described in more detail below with respect to FIGS. 2-4, the liquid agent pressure and flow rate as well as the duration of the injector valve opening time may all be independently controlled and used in a feedback control routine to precisely control the mass of liquid injected. Additionally, the mixed medical gas/agent may be passed through an agent concentration sensor that provides feedback to control the valve opening time, pump speed, and/or outlet pressure. The system may use a closed loop feedback control for precise agent control, as well as a backup and check by calculating valve opening vs. closed time over a given time frame, and together with knowledge of the agent temperature and pressure, a rationality check on agent delivery is provided. This may also serve as a backup control method should component degradation, such as to the concentration sensor, occur. It may also be used to indicate sensor drift, which may be compensated for by apply a correction factor, for example.

Figure 2:
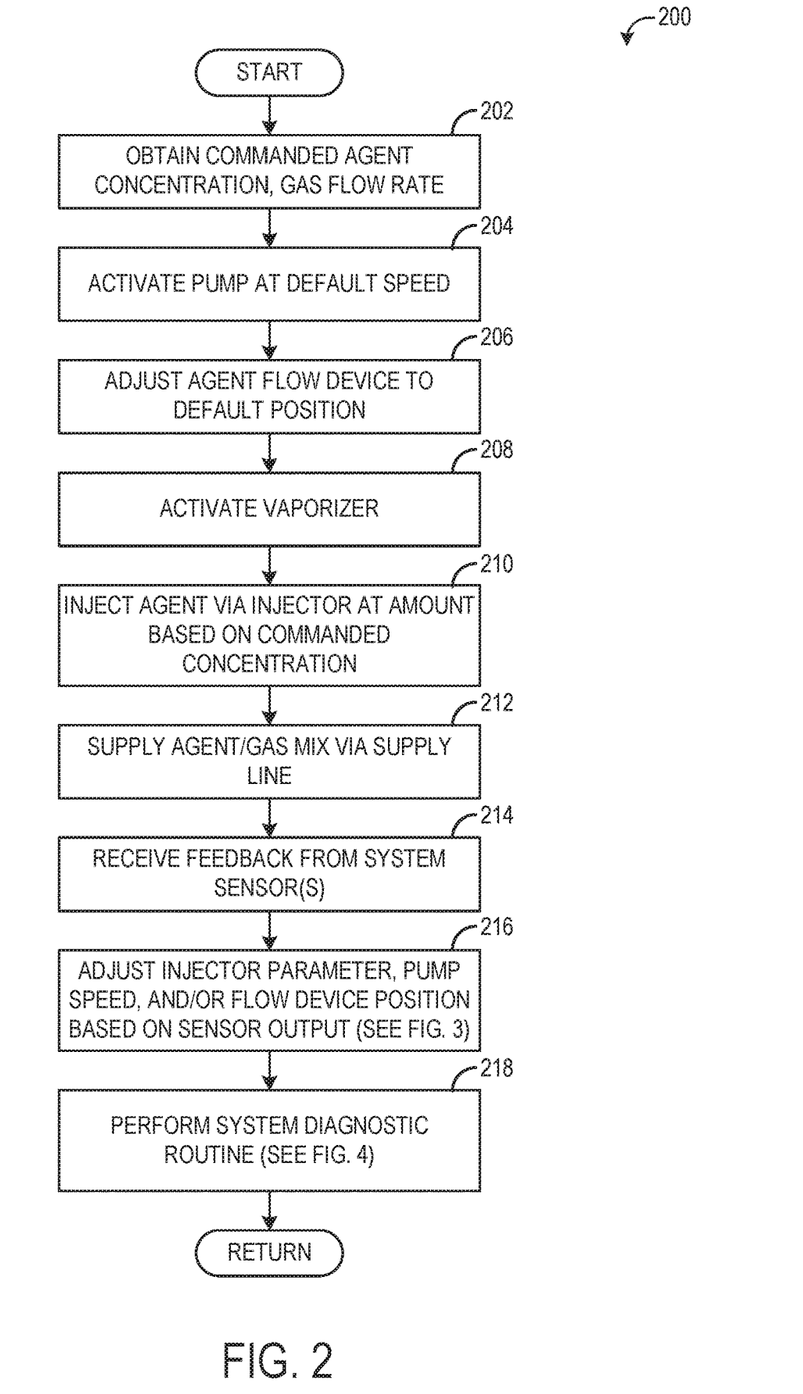
FIG. 2 is a flow chart illustrating a method for operating an anesthetic agent delivery system.

Turning now to FIG. 2, a method 200 for operating an anesthetic agent delivery system, such as the system 100 of FIG. 1, is shown. Method 200 may be carried out according to instructions stored in memory of a controller, such as controller 118 of FIG. 1, in conjunction with one or more sensors (e.g., sensors 120, 122, 124, 126, 128, 130, and/or 132 of FIG. 1) and actuators (e.g., pump 104, injector 106, and/or flow control device 112 of FIG. 1).

At 202, method 200 includes obtaining a commanded agent concentration and medical gas flow rate. The agent may be a suitable anesthetic agent, such as desflurane, isoflurane, halothane, or the like. The commanded agent concentration may include a percentage of the vaporized agent per volume of a medical gas/agent mix provided to a patient. The commanded agent concentration may be obtained via user input to the controller or other suitable mechanism.

At 204, method 200 includes activating the pump at a default speed. The default speed may be a predetermined speed stored in memory of the controller that may quickly increase the pressure of the liquid agent in the liquid agent supply line to a target pressure. At 206, method 200 includes adjusting the agent flow control device to a default position. The default position may initially include a closed position until the pressure of the liquid agent in the return line (or in the liquid agent supply line) reaches a threshold pressure, at which time the flow control device may be opened. In some examples, the pump speed and/or agent flow valve position may be determined based on a desired or commanded rail pressure (e.g., injector inlet pressure). For example, a desired flow rate may be compared to a curve that plots injector flow as a function of pressure. Based on a desired injection duty cycle, the pressure may be determined.

At 208, a vaporizer is activated, such as vaporizer 114 of FIG. 1. Activating the vaporizer may include activating a heat source of the vaporizer to heat the vaporization chamber to a target temperature. Further, activating the vaporizer may include flowing medical gas into the vaporizer. At 210, the agent is injected into the vaporizer via the injector. Initially, the injector may inject an amount of agent that is based on the commanded agent concentration, e.g., an amount predicted to result in the commanded agent concentration being reached. The amount of injected agent may be controlled by controlling the duty cycle of the injector, where the duty cycle represents a percentage of time the injector is open for a given period of time. The duty cycle frequency may be adjusted and/or an open duration of the open periods of the duty cycle may be adjusted. Additionally or alternatively, the amount of injected agent may be controlled by controlling a valve position of the injector, such as a degree of opening of the injector. As explained previously, the injected liquid agent may vaporize in the vaporizer and mix with the supplied medical gas. In an example, the injection frequency (e.g., duty cycle) may include a maximum frequency that is set based on a desired lifetime of the injector (e.g., the higher the frequency, the lower the lifetime). The injection duration may include a minimum injection duration that is limited by valve speed and fluid dynamics. A desired injection parameter setpoint (e.g., desired injection frequency and/or duration) may be limited by the maximum frequency and minimum duration.

At 212, method 200 includes supplying the vaporized agent/medical gas mix to a patient via a supply line. At 214, method 200 includes receiving feedback from one or more system sensors. Such sensors may include the agent concentration sensor (e.g., sensor 132) that measures a concentration of the agent in the agent/medical gas mix, as well as sensors that measure a differential pressure across the injector (e.g., sensors 124 and 128), liquid agent pressure (e.g., sensor 124), liquid agent temperature (e.g., sensor 126), agent/medical gas mix flow rate (e.g., sensor 130), and gas temperature (e.g., sensor 131).

At 216, method 200 includes adjusting one or more injector parameters, a pump speed, and/or a flow control device position based on the sensor output. The adjustment to the actuators of the anesthetic agent delivery system based on the sensor output will be discussed in more detail below with respect to FIG. 3. At 218, method 200 optionally includes performing a system diagnostic routine, which will be explained in more detail below with respect to FIG. 4.

Figure 3:
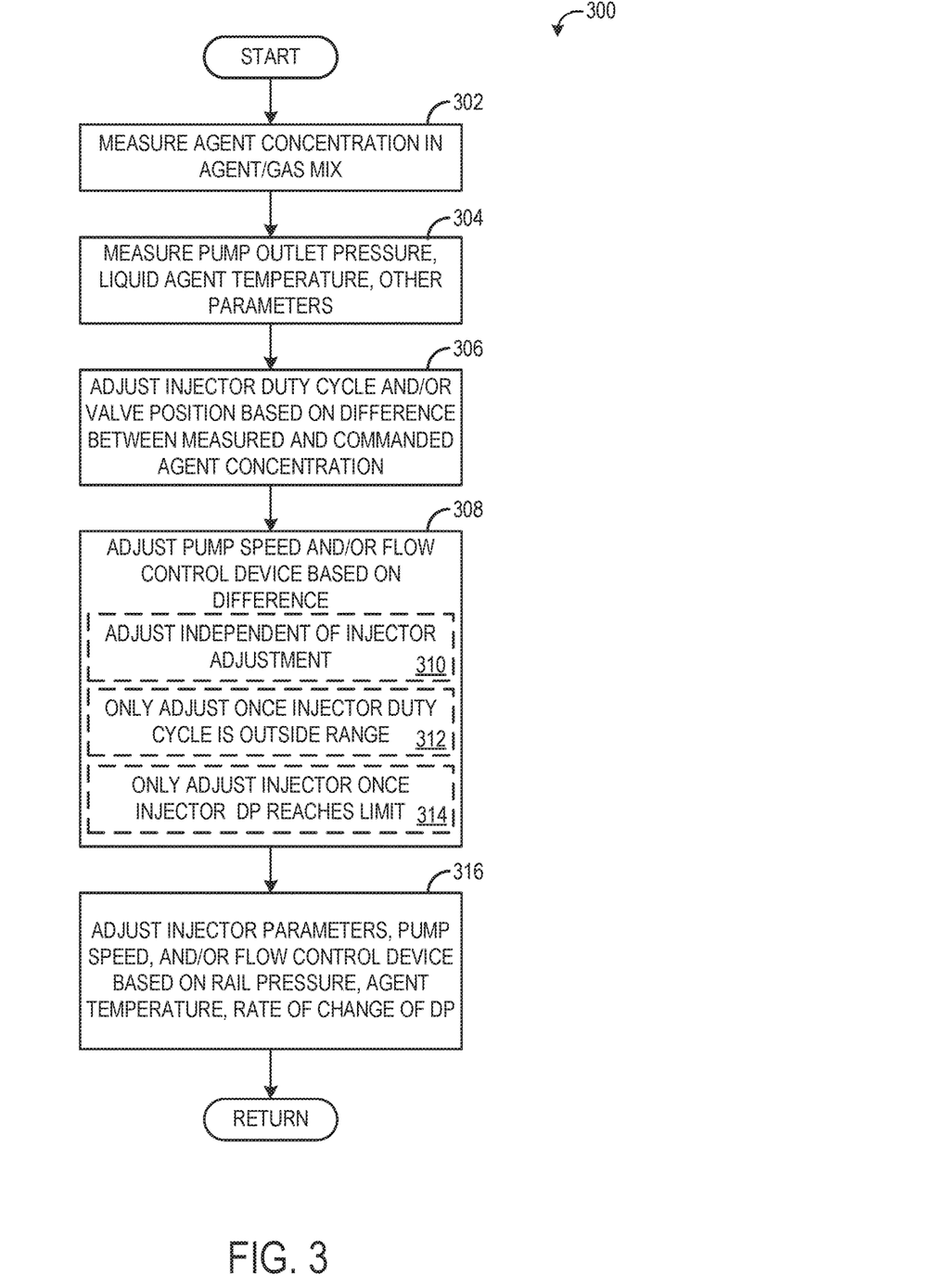
FIG. 3 is a flow chart illustrating a method for adjusting one or more anesthetic agent delivery system components in response to feedback from one or more sensors of the anesthetic agent delivery system.

FIG. 3 illustrates a method 300 for adjusting one or more anesthetic agent delivery system components in response to feedback from one or more sensors of the anesthetic agent delivery system. Method 300 may be performed as part of method 200, for example after the pump, injector, and vaporizer have been activated. At 302, method 300 includes measuring the concentration of the agent in the vaporized agent/medical gas mix. The concentration may be measured with a concentration sensor (e.g., sensor 132) positioned in a supply line configured to supply the vaporized agent/medical gas mix from the vaporizer to a patient. Additionally, in some examples, parameters of the anesthetic agent/medical gas mix may be measured and used along with the concentration. For example, the temperature and/or flow rate of the anesthetic agent/medical gas mix may be used along with the output from the concentration sensor to determine the concentration of the vaporized agent, as the gas temperature may contribute noise to the concentration measurement, for example. At 304, method 300 includes measuring pump outlet pressure and liquid agent temperature. The pump outlet pressure may be measured with a pressure sensor (e.g., sensor 124) positioned in a liquid agent supply line intermediate the pump and injector. The liquid agent temperature may be measured with a temperature sensor (e.g., sensor 126) positioned in the liquid agent supply line intermediate the pump and injector. Additional sensor output may be obtained, including but not limited to vaporized agent/medical gas mix flow rate (e.g., from sensor 130), vaporizer pressure (e.g., from sensor 128), pump speed (e.g., from sensor 122), and agent reservoir pressure (e.g., from sensor 120).

At 306, method 300 includes adjusting injector duty cycle and/or valve position based on a difference between the measured agent concentration and commanded agent concentration. For example, if the measured agent concentration is less than the commanded agent concentration, the injector duty cycle may be increased to increase the mass of agent injected into the vaporizer. In some examples, the mass of agent to be injected in order to reach the commanded agent concentration may be determined as a function of the mass flow of the vaporized agent/medical gas mix, and the duty cycle (or valve position) command may be based on this determined mass. In an example, the difference between the measured and commanded agent concentrations (also referred to as the error) may be input into a PID controller to determine an injector duty cycle or valve position command.

At 308, method 300 includes adjusting the pump speed and/or flow control device position based on the difference between the measured and commanded agent concentrations. In one example, adjusting the pump speed and/or flow control device position based on the difference includes adjusting the pump speed and/or flow control device position independently of the adjustment to the injector duty cycle or valve position, as indicated at 310. For example, the difference between the measured and commanded agent concentrations may be input into a PID controller that outputs independent injector duty cycle (or valve position), pump speed, and flow control device position commands.

In another example, the adjustments to the pump speed and/or flow control device position may be performed in a manner that results in the injector valve duty cycle frequency remaining within a threshold range. Since the frequency of the injector being cycled open and closed directly effects wear and hence injector life, the frequency may be adjusted by adjusting the differential pressure across the injector, for example to achieve nearly 100% open time. However, a suitable margin below 100% may be used to allow for control for variation from noise parameters (explained in more detail below). Thus, in one example, the differential pressure may be controlled such that the frequency of injector cycling can be held within a desired design range to maintain injector life, e.g. 50%<f<85%.

As such, adjusting the pump speed and/or flow control device position based on the difference may include only adjusting the pump speed and/or flow control device position once the injector duty cycle is outside the threshold range (e.g., where the threshold range is 50%-85%), as indicated at 312. In this way, the mass of injected agent may be adjusted by first adjusting the duty cycle of the injector. Then, if the duty cycle of the injector drops to below 50%, for example, the pump speed and/or flow control device position may be adjusted, in order to adjust the differential pressure across the injector and hence the mass of agent injected by the injector.

In another example, adjusting the pump speed and/or flow control device position based on the difference may include only adjusting the injector once the differential pressure across the injector reaches a limit, as indicated at 314. For example, when the difference is greater than or less than zero, the mass of injected agent may be adjusted by first adjusting the pump speed and/or flow control device to adjust the differential pressure across the injector. Once the differential pressure reaches a limit (such as a maximum differential pressure allowable by the system due to valve position saturation, pump speed saturation, or component pressure limits, or a minimum differential pressure that still sustains injection and vaporization of the agent), then the injector duty cycle may be adjusted.

Additionally, the density and viscosity of the liquid agent may fluctuate due to ambient temperature changes, for example, which introduces noise into the control scheme discussed above. For example, the difference between the measured and commanded agent concentration may at least in part be due to a change in liquid agent temperature. Thus, the liquid agent supply line pressure, pump speed, and/or injector state may be adjusted to compensate the fluid density and viscosity changes due to temperature to compensate for changes in the mass flow rate through the injector due to agent property changes.

Accordingly, at 316, method 300 includes adjusting injector parameters (such as duty cycle or valve position), pump speed, and/or flow control device position based on agent rail pressure (e.g., the pressure downstream of the pump/upstream of the injector as detected by sensor 124, for example), liquid agent temperature, and/or a rate of change of differential pressure across the injector. Method 300 then returns.

Thus, method 300 of FIG. 3 may adjust the amount of injected anesthetic agent based on an error between a measured agent concentration and a commanded agent concentration. The amount of injected anesthetic agent may be adjusted by adjusting one or both of an injection frequency (e.g., how often the injector is opened in a given period of time) and an injection duration (e.g., how long the injector is open during a given injection event). The injection frequency and duration are defined by a desired state. Lower frequency may result in a longer valve life, while a higher frequency may result in better accuracy of reaching the commanded agent concentration. As such, a maximum frequency may be set based on a desired field life of the valve. The maximum flow rate through the valve is determined by the pressure across the valve. The desired flow rate may be set to be less than the maximum valve flow rate that the valve is capable of achieving. From the desired flow rate, a pressure is set by selection of a desired frequency or duration (where typical duty cycle values may be 20%<duty cycle<80%). This sets the percentage of total valve open time, and the frequency is then determined by the desired on time per injection cycle. As an example, if the duty cycle is set to 30%, then over a minute the valve would be open 0.3*60 s or 18 s. Over that minute period a frequency is selected to sub-divide the injector on times into segments, for example such that a 1 Hz frequency (which includes 60 on/off cycles in a minute) results in the valve staying open 18/60=0.3 secs, then closed for 0.7 sec.

Figure 4:
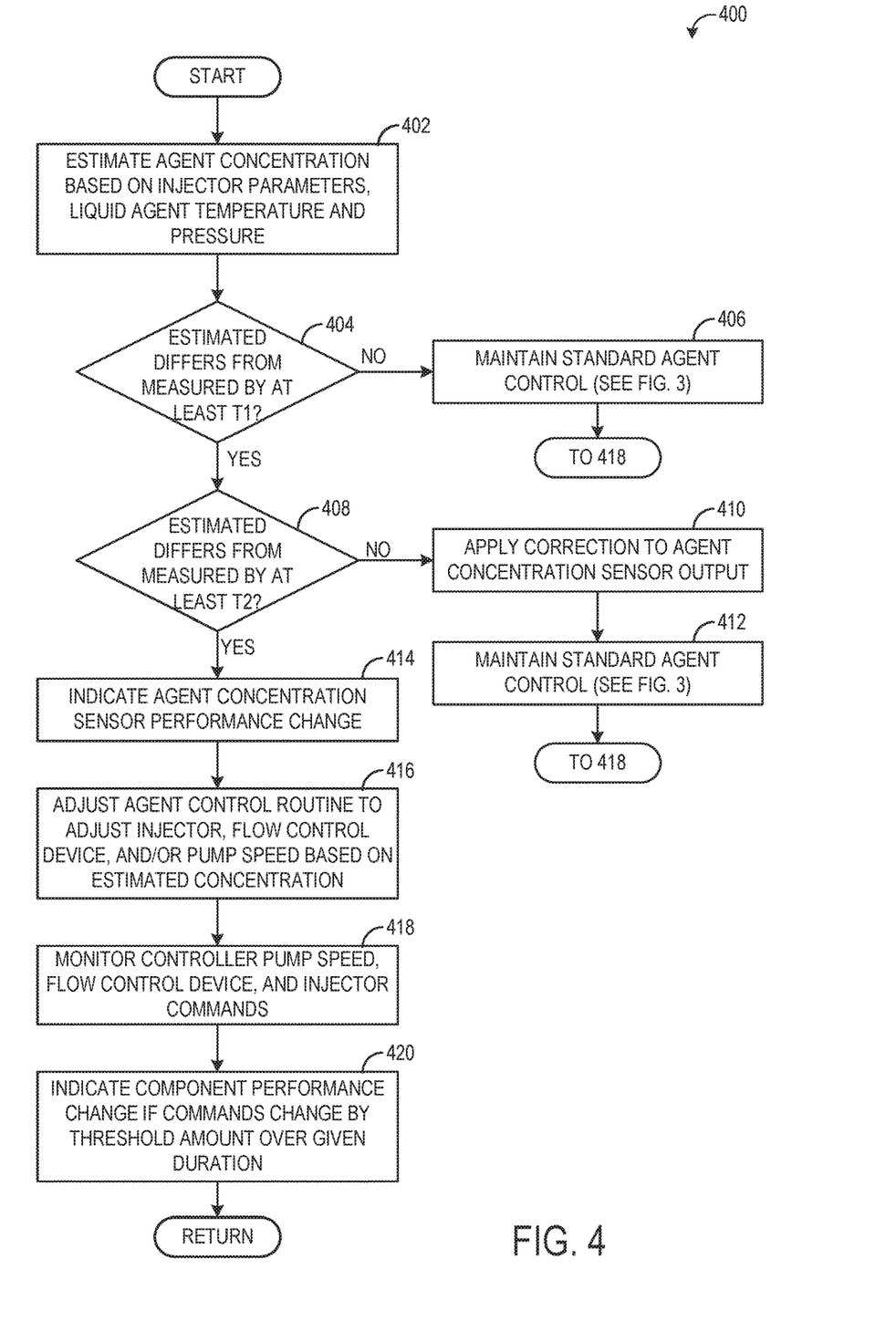
FIG. 4 is a flow chart illustrating a method for performing a diagnostic of an anesthetic agent delivery system.

FIG. 4 illustrates a method 400 for diagnosing an anesthetic agent delivery system, such as the system 100 of FIG. 1. Method 400 may be performed as part of method 200, for example once all system components are activated and anesthetic agent is being delivered to a patient. Method 400 may be performed in parallel with method 300, at least in some examples.

At 402, method 400 estimates a concentration of the vaporized anesthetic agent in the vaporized agent/medical gas mix supplied to the patient. The agent concentration may be estimated based on injector parameters (such as duty cycle and valve open position), liquid agent temperature, and liquid agent pressure. The liquid agent temperature and pressure may be determined from output from temperature and pressure sensors positioned between the pump and the injector, e.g., sensors 124 and 126. The injector parameters may be obtained by the controller as the commanded injector duty cycle and valve position sent to the injector. The injector flow rate when the valve is open may be estimated from the measured pressure difference across the valve and a valve characteristic pressure difference vs. a flow curve (generated from either generalized average data or specific to given injector in system). By knowing the agent temperature and pressure and duration/frequency/amount of the injector opening, the mass flow through the injector may be estimated and the agent concentration estimated from the mass flow of the agent through the injector and mass flow of the agent/medical gas mix.

At 404, method 400 includes determining if the estimated concentration differs from the measured concentration by at least a first threshold amount. The measured concentration may be measured by the concentration sensor (e.g., sensor 132). The first threshold amount may be an amount that indicates concentration sensor drift is starting occur, where below the first threshold amount, the sensor is determined to be healthy and above the threshold amount, a correction may be applied to the sensor output to ensure accurate feedback control of the agent concentration is maintained. The first threshold amount may be a suitable amount, such as a difference of 10%.

If the estimated concentration does not differ from the measured by concentration by at least the first threshold, method 400 proceeds to 406 to maintain standard agent concentration control, as described above with respect to FIG. 3. Method 400 then proceeds to 418, explained in more detail below.

If the estimated concentration does differ from the measured concentration by at least the first threshold, method 400 proceeds to 408 to determine if the estimated concentration differs from the measured concentration by at least a second threshold. The second threshold may be larger than the first threshold, and may be a suitable value such as 25%. A difference greater than the second threshold may indicate concentration sensor change in performance.

If the estimated concentration does not differ from the measured concentration by at least the second threshold, method 400 proceeds to 410 to apply a correction to the output of the agent concentration sensor. As explained above, the agent concentration sensor may experience drift over time. The amount the sensor output has drifted may be determined and the drift may be compensated for by correcting the output of the sensor, so that accurate agent concentration may still be determined. At 412, method 400 includes maintaining the standard agent control as described above with respect to FIG. 3, albeit using corrected agent sensor output. Method 400 then proceeds to 418, explained below.

If the estimated concentration does differ from the measured concentration by at least the second threshold, method 400 proceeds to 414 to indicate agent concentration sensor performance change. The performance change may be indicated by storing a diagnostic code in the controller, outputting a notification to a user of the anesthetic agent delivery system, or other suitable indication. At 416, method 400 includes adjusting the agent control routine to adjust injector parameter(s), flow control device, and/or pump speed based on the estimated agent concentration. For example, the amount of injected agent may be controlled according to the method 300 of FIG. 3, but rather than use the measured agent concentration, the estimated agent concentration may be used to adjust the injector parameters, pump speed, and/or flow control device position.

At 418, method 400 monitors the pump speed, flow control device position, and injector commands output by the controller. The commands may be monitored over time and compared to expected commands based on the commanded agent concentration and agent/medical gas mix flow rate. The expected commands may be determined with a fresh (e.g., new) anesthetic agent delivery system and stored in memory of the controller. In some examples, the expected commands may be updated over time as the system is used to reflect wear to the system.

At 420, method 400 includes indicating component change in performance if one or more of the commands changes by a threshold amount over a given duration. For example, if the injector duty cycle command for a given commanded agent concentration and mass flow changes by at least 25% over a duration (such as a week or a month), injector valve performance change may be indicated. The indication may include storing a diagnostic code and/or notifying a user. Method 400 then returns.

Thus, a rationality check of the injector and other components as function of input parameters may be performed to provide a secondary check and fallback agent delivery method in case of an agent concentration sensor that is operating with reduced performance. The rationality check may also be used as a check on agent concentration sensor drift. And inversely, by observing variations in the controller output compared to calibration values, injector wear or blockage may be detected. Further, in some examples, rather than relying on one-time comparisons to threshold values to determine component degradation (e.g., where concentration sensor degradation is indicated based on the difference between the measured agent concentration and the estimated agent concentration being greater than the second threshold), the controller may additionally or alternatively track and trend the number of times the system has demonstrated a reduced performance. For example, when the difference between the measured agent concentration and the estimated agent concentration exceeds the first threshold but does not exceed the second threshold, the number of times difference exceeds the first threshold may be stored and updated. Once the number of times exceeds a threshold, the sensor may be indicated as exhibiting reduced performance. In another example, the difference may be monitored over time to determine a trend in the difference. For example, the difference may increase over time and based on the rate of change of the difference, sensor performance reduction may be indicated.

In some examples, the model-based control described above with respect to FIG. 4 (e.g., where the agent concentration is estimated) may be utilized instead of the measurement-based control, for example in systems where the concentration sensor is omitted. For example, a look-up table stored in memory of the controller may include one or more of injector duty cycle, injector valve open position, liquid agent temperature, and liquid agent pressure as inputs and may output an estimated agent concentration that may be used to determine an error signal that controls the duty cycle of the injector, for example. In another example, the commanded agent concentration may be entered into a look-up table along with one or more system parameters (e.g., current injector duty cycle, current injector valve open position, liquid agent temperature, and/or liquid agent pressure) in order to obtain a commanded injector duty cycle.

The methods and system described herein provide for an anesthetic agent system that utilizes a liquid pump combined with an injector valve to control the amount of anesthetic agent injected into gas stream inhaled by a patient. The liquid pump pressure, flow rate, and valve opening time are used together with feedback from a gas concentration sensor to precisely management the amount of agent injected. The closed loop control described herein provides precise input of anesthetic agent, reducing agent usage during a procedure and also provides rapid adjustment of anesthetic agent, including no residual agent bolus to be consumed when the injector is closed.

In order to control the injector valve output flow rate as described herein, the injector valve open/close on—off time may be controlled. Additionally or alternatively, the injector open time duration may be controlled, with the injector opened at fixed frequency. Additionally or alternatively, both the frequency and open time duration may be controlled and/or the injector valve position may be controlled. Additionally or alternatively, the pump speed may be controlled to adjust the pressure in front of the injector. Additionally or alternatively, the pump outlet pressure may be controlled via control of the flow control device, which acts as a pressure regulator.

The system described herein may provide many advantages. Because the agent reservoir is not pressurized, the reservoir can be re-filled with agent without shutting off the vaporizer, enabling "fill on the fly" and eliminating need for reservoir depressurization. The system also enables a-model based injector control to calculate agent flow rate in cases where the agent concentration sensor is exhibiting reduced performance. Further, the use of the differential pressure control coupled with frequency control of the injector may be used to increase injector life by reducing the number of cycles compared to just frequency control. Additionally, the system eliminates the need for a separate mixer and gas by-pass through vaporizer, reducing plumbing and valves.

A technical effect a pressurized liquid anesthetic agent delivery system is precise control of delivered anesthetic agent that can be adjusted nearly-instantaneously and can account for noise influenced by agent temperature, pressure fluctuations, or other contributing factors (e.g., vibration, altitude, atmospheric conditions).

An example provides for a system for delivering an anesthetic agent. The system includes an anesthetic agent reservoir; a pump fluidically coupled to the agent reservoir; an injector configured to receive pressurized anesthetic agent from the pump; a vaporizer comprising a heated chamber configured to receive and vaporize the anesthetic agent injected by the injector and supply a mix of the vaporized anesthetic agent and medical gas to a subject via a supply line; and a controller. The controller stores instructions executable to determine a concentration of the vaporized anesthetic agent in the mix; and adjust one or more injector parameters based on a difference between the concentration of the vaporized anesthetic agent and a commanded concentration.

In an example, the system further includes an anesthetic agent concentration sensor positioned in the supply line, and the instructions are executable to determine the concentration of the vaporized anesthetic agent in the mix based on output from the anesthetic agent concentration sensor. In some examples, the concentration of the vaporized anesthetic agent in the mix may be further determined based on output from a temperature sensor positioned upstream of the concentration sensor. In examples, the one or more injector parameters may include one or more of injector duty cycle frequency, open duration, and injector valve position. In examples, the instructions are executable to further adjust the one or more injector parameters based on a pressure drop across the injector. In examples, the instructions are executable to further adjust the one or more injector parameters based on one or more of a pressure of the reservoir, a temperature of the agent upstream of the injector, and a rate of change of the pressure drop across the injector. In examples, the instructions are executable to adjust a speed of the pump based on the difference. In examples, the system further includes an agent flow device positioned in a return line fluidically coupled between the injector and the reservoir, and the instructions are executable to adjust a position of the agent flow device based on the difference. In some examples, the agent flow device may be a valve. In examples, the one or more injector parameters comprise a duty cycle frequency of the injector, and the instructions are executable to adjust the duty cycle frequency based on the difference, and when the duty cycle frequency falls below a threshold frequency, adjust the position of the agent flow device. In examples, the system further includes an interface fluidically coupled to the anesthetic agent reservoir, the interface configured fluidically connect a liquid anesthetic agent commercial container to the anesthetic agent reservoir.

Another example provides for a system for delivering an anesthetic agent, the system including an anesthetic agent reservoir; a pump fluidically coupled to the agent reservoir; an injector configured to receive pressurized anesthetic agent from the pump; a vaporizer comprising a heated chamber configured to receive and vaporize the anesthetic agent injected by the injector and supply a mix of the vaporized anesthetic agent and medical gas to a subject via a supply line; and a controller storing instructions executable to estimate a concentration of the vaporized anesthetic agent in the mix based on a duty cycle of the injector, a temperature of the anesthetic agent, and a pressure of the anesthetic agent; and adjust one or more injector parameters based on the estimated concentration.

In examples, the system further includes an anesthetic agent concentration sensor positioned in the supply line, and the one or more injector parameters are adjusted based on the estimated concentration in response to an indication that the anesthetic agent concentration sensor is exhibiting reduced performance. In some examples, the reduced performance may include the sensor being degraded. In examples, the instructions are executable to indicate that the anesthetic agent concentration sensor is exhibiting reduced performance responsive to the estimated concentration differing from a measured concentration of the vaporized anesthetic agent in the mix (as measured by the anesthetic agent concentration sensor) by a threshold amount. In examples, the one or more injector parameters include one or more of injector duty cycle frequency, open duration, and injector valve position. In examples, the instructions are executable to adjust the one or more injector parameters based on the estimated concentration by determining a difference between the estimated concentration and a commanded agent concentration, the commanded agent concentration determined from user input and adjusting the one or more injector parameters based on the difference. In examples, the system further includes an interface fluidically coupled to the anesthetic agent reservoir, the interface configured fluidically connect a liquid anesthetic agent commercial container to the anesthetic agent reservoir.

Another example provides for a system for delivering an anesthetic agent, the system including an anesthetic agent reservoir; a pump fluidically coupled to the agent reservoir; an injector configured to receive pressurized anesthetic agent from the pump; a return line fluidically coupling the injector to the reservoir, an agent flow control device positioned in the return line; a vaporizer comprising a heated chamber configured to receive and vaporize the anesthetic agent injected by the injector and supply a mix of the vaporized anesthetic agent and medical gas to a subject via a supply line; an anesthetic agent concentration sensor positioned in the supply line; and a controller. The controller stores instructions executable to determine a concentration of the vaporized anesthetic agent in the mix based on output from the anesthetic agent concentration sensor; perform a first adjustment of one or more injector parameters based on a difference between the concentration of the vaporized anesthetic agent and a commanded concentration; perform a second adjustment of the agent flow control device based on the difference; and perform a third adjustment of a speed of the pump based on the difference.

In examples, the instructions are executable to further adjust the one or more injector parameters based on one or more of a pressure of anesthetic agent reservoir, a temperature of the pressurized anesthetic agent upstream of the injector, and a rate of change of a differential pressure across the injector. In examples, the one or more injector parameters comprise one or more of injector duty cycle frequency, open duration, and injector valve position. In examples, the system further includes an interface fluidically coupled to the anesthetic agent reservoir, the interface configured fluidically connect a liquid anesthetic agent commercial container to the anesthetic agent reservoir.

In another representation, a method includes injecting liquid anesthetic agent to a vaporizer via an injector, supplying a mix of vaporized anesthetic agent and medical gas to a subject via a supply line coupled to the vaporizer, determining a concentration of vaporized anesthetic agent in the mix, and adjusting one or more parameters of the injector based on a difference between the concentration of the vaporized anesthetic agent and a commanded concentration.

In another representation, a method includes injecting liquid anesthetic agent to a vaporizer via an injector, supplying a mix of vaporized anesthetic agent and medical gas to a subject via a supply line coupled to the vaporizer, estimating a concentration of the vaporized anesthetic agent in the mix based on a duty cycle of the injector, a temperature of the anesthetic agent, and a pressure of the anesthetic agent, and adjusting one or more injector parameters based on the estimated concentration.

In another representation, a method includes injecting liquid anesthetic agent to a vaporizer via an injector, the injector provided with liquid anesthetic agent from a reservoir via a pump, supplying a mix of vaporized anesthetic agent and medical gas to a subject via a supply line coupled to the vaporizer, determining a concentration of the vaporized anesthetic agent in the mix based on output from an anesthetic agent concentration sensor, performing a first adjustment of one or more injector parameters based on a difference between the concentration of the vaporized anesthetic agent and a commanded concentration, performing a second adjustment of an agent flow control device based on the difference, and performing a third adjustment of a speed of the pump based on the difference.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A system for delivering an anesthetic agent, comprising:
  an anesthetic agent reservoir;
  a pump fluidically coupled to the agent reservoir;
  an injector configured to receive pressurized anesthetic agent from the pump, the injector comprising a plurality of nozzle holes;
  a vaporizer comprising a heated chamber configured to receive and vaporize the anesthetic agent injected by the injector via the plurality of nozzle holes and supply a mix of the vaporized anesthetic agent and medical gas to a subject via a supply line; and
  a controller storing instructions executable to:
    determine a concentration of the vaporized anesthetic agent in the mix;
    and adjust one or more injector parameters including at least a duty cycle of the injector based on a difference between the concentration of the vaporized anesthetic agent and a commanded concentration;
    wherein the one or more injector parameters further comprise one or more of injector open duration and injector valve position;

and an agent flow valve positioned in a return line fluidically coupled between the injector and the agent reservoir;
and wherein the instructions are further executable to:
first adjust the duty cycle based on the difference, and responsive to the duty cycle falling below a threshold, adjust the position of the agent flow valve.

2. The system of claim 1, further comprising an anesthetic agent concentration sensor positioned in the supply line, and wherein the instructions are executable to determine the concentration of the vaporized anesthetic agent in the mix based on output from the anesthetic agent concentration sensor.

3. The system of claim 1, wherein the instructions are executable to further adjust the one or more injector parameters based on a pressure drop across the injector.

4. The system of claim 3, wherein the instructions are executable to further adjust the one or more injector parameters based on one or more of a pressure of the agent reservoir, a temperature of the anesthetic agent upstream of the injector, and a rate of change of the pressure drop across the injector.

5. The system of claim 1, wherein the instructions are executable to adjust a speed of the pump based on the difference, and wherein adjusting at least the duty cycle based on the difference comprises if the concentration of the vaporized anesthetic agent is less than the commanded concentration, increasing the duty cycle.

6. The system of claim 1, wherein the duty cycle comprises a percentage of a given period of time that the injector is open, wherein a duty cycle frequency comprises a frequency at which the injector is opened for the given period of time, and wherein the instructions are executable to adjust one or both of the duty cycle frequency and the injector open duration to reach the duty cycle.

7. The system of claim 1, further comprising an interface fluidically coupled to the agent reservoir, the interface configured to fluidically connect a liquid anesthetic agent commercial container to the anesthetic agent reservoir.

8. A system for delivering an anesthetic agent, comprising:
an anesthetic agent reservoir;
a pump fluidically coupled to the agent reservoir;
an injector configured to receive pressurized anesthetic agent from the pump;
a vaporizer comprising a heated chamber configured to receive and vaporize the anesthetic agent injected by the injector and supply a mix of the vaporized anesthetic agent and medical gas to a subject via a supply line; and
a controller storing instructions executable to:
estimate a concentration of the vaporized anesthetic agent in the mix based on a duty cycle of the injector, a temperature of the anesthetic agent, and a pressure of the anesthetic agent; and
adjust one or more injector parameters based on the estimated concentration.

9. The system of claim 8, further comprising an anesthetic agent concentration sensor positioned in the supply line, and wherein the one or more injector parameters are adjusted based on the estimated concentration in response to an indication that the anesthetic agent concentration sensor is exhibiting reduced performance.

10. The system of claim 9, wherein the instructions are executable to indicate that the anesthetic agent concentration sensor is exhibiting reduced performance responsive to the estimated concentration differing from a measured concentration of the vaporized anesthetic agent in the mix as measured by the anesthetic agent concentration sensor by a first threshold amount, and wherein the instructions are further executable to:
if the difference between the measured concentration and the estimated concentration is less than the threshold amount but greater than a second threshold amount, correct output from the anesthetic agent concentration sensor and adjust one or more injector parameters based on the corrected output.

11. The system of claim 8, wherein the one or more injector parameters comprise one or more of injector duty cycle frequency, open duration, and injector valve position.

12. The system of claim 8, wherein the instructions are executable to adjust the one or more injector parameters based on the estimated concentration by determining a difference between the estimated concentration and a commanded agent concentration, the commanded agent concentration determined from user input and adjusting the one or more injector parameters based on the difference.

13. The system of claim 8, further comprising an interface fluidically coupled to the agent reservoir, the interface configured to fluidically connect a liquid anesthetic agent commercial container to the agent reservoir.

14. A system for delivering an anesthetic agent, comprising:
an anesthetic agent reservoir;
a pump fluidically coupled to the agent reservoir;
an injector configured to receive pressurized anesthetic agent from the pump;
a return line fluidically coupling the injector to the agent reservoir, an agent flow control device positioned in the return line;
a vaporizer comprising a heated chamber configured to receive and vaporize the anesthetic agent injected by the injector and supply a mix of the vaporized anesthetic agent and medical gas to a subject via a supply line;
an anesthetic agent concentration sensor positioned in the supply line; and
a controller storing instructions executable to:
determine a concentration of the vaporized anesthetic agent in the mix based on output from the anesthetic agent concentration sensor;
perform a first adjustment of one or more injector parameters based on a difference between the concentration of the vaporized anesthetic agent and a commanded concentration;
perform a second adjustment of the agent flow control device based on the difference; and
perform a third adjustment of a speed of the pump based on the difference; wherein the one or more injector parameters comprise injector duty cycle frequency; and wherein the instructions are further executable to:
perform the first adjustment until a threshold injector duty cycle is reached, and then perform the second adjustment and the third adjustment.

15. The system of claim 14, wherein the instructions are executable to further adjust the one or more injector parameters based on one or more of a pressure of the agent reservoir, a temperature of the pressurized anesthetic agent upstream of the injector, and a rate of change of a differential pressure across the injector.

16. The system of claim 14, further comprising an interface fluidically coupled to the agent reservoir, the interface configured to fluidically connect a liquid anesthetic agent commercial container to the agent reservoir.

17. The system of claim 14, wherein the instructions are executable to perform the second adjustment and the third adjustment until a threshold pressure differential across the injector is reached, and then perform the first adjustment.

* * * * *